(12) United States Patent
Dhurandhar et al.

(10) Patent No.: US 11,009,494 B2
(45) Date of Patent: May 18, 2021

(54) PREDICTING HUMAN DISCRIMINABILITY OF ODOR MIXTURES

(71) Applicant: International Business Machines Corporation, Armonk, NY (US)

(72) Inventors: Amit Dhurandhar, Yorktown Heights, NY (US); Guillermo Cecchi, New York, NY (US); Pablo Meyer Rojas, Brooklyn, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 336 days.

(21) Appl. No.: 16/121,100

(22) Filed: Sep. 4, 2018

(65) Prior Publication Data

US 2020/0072808 A1    Mar. 5, 2020

(51) Int. Cl.
*G01N 33/00* (2006.01)
*G16C 20/30* (2019.01)
(Continued)

(52) U.S. Cl.
CPC ......... *G01N 33/0073* (2013.01); *G16C 20/30* (2019.02); *G16C 20/90* (2019.02); *G06N 5/022* (2013.01); *G06Q 30/0631* (2013.01)

(58) Field of Classification Search
CPC .. G01N 33/0073; G06N 5/022; G06F 19/704; G06Q 30/0631; G16C 20/30
See application file for complete search history.

(56) References Cited

U.S. PATENT DOCUMENTS 9,140,677 B2 * 9/2015 Mershin ............. G01N 33/0031
9,176,104 B2 11/2015 Haddad et al.
(Continued)

FOREIGN PATENT DOCUMENTS

WO  2013035070  3/2013
WO  2014111611  7/2014

OTHER PUBLICATIONS

Priebe, 'Olfactory Classification via Inter-point Distance Analysis', Apr. 2001, IEEE Publication, vol. 23, pp. 404-413 (Year: 2001).*
(Continued)

*Primary Examiner* — Elias Desta
(74) *Attorney, Agent, or Firm* — Amin, Turocy & Watson, LLP

(57) ABSTRACT

A system for compressing data during neural network training, comprising of memory that stores computer executable components; a processor that executes computer executable components stored in the memory, wherein the computer executable components comprise of a compilation component that compiles respective molecular descriptors regarding a first set of molecules; a perception component that learns human perception information related to olfactory perceptions of the first set of molecules, and generates predictions of human olfactory perceptions of a second set of molecules; a fitting component that fits distance predictions from the perception component regarding the second set of molecules against measured correct classifications regarding the second set of molecules; and a vector component that generates a perceptual vector distance between two olfactory targets.

20 Claims, 7 Drawing Sheets

(51) Int. Cl.
*G16C 20/90* (2019.01)
*G06Q 30/06* (2012.01)
*G06N 5/02* (2006.01)

(56) References Cited

U.S. PATENT DOCUMENTS

| | | |
|---|---|---|
| 9,959,392 B2 | 5/2018 | Sobel et al. |
| 2016/0091470 A1 | 3/2016 | Gafsou |
| 2017/0364605 A1 | 12/2017 | Sobel et al. |
| 2018/0089739 A1 | 3/2018 | Cecchi et al. |

OTHER PUBLICATIONS

Aeloor et al., 'A survey on Odor Detection Sensors', 2017, IEEE Publication, pp. 1-5 (Year: 2017).*
Keller et al., "Predicting human olfactory perception from chemical features of odor molecules," ResearchGate, Science Magazine, Feb. 27, 2017, 9 pages.
Snitz et al., "Predicting odor perceptual similarity from odor structure," PLOS Computational Biology, vol. 9, Issue 9, Sep. 2013, 12 pages.

* cited by examiner

PREDICTING HUMAN DISCRIMINABILITY OF ODOR MIXTURES

TECHNICAL FIELD

The subject disclosure relates generally to a neural network based model that can predict perceptual olfactory qualities of molecular mixtures and perceptual distance between odor mixtures based on structural properties.

SUMMARY

The following presents a summary to provide a basic understanding of one or more embodiments of the invention. This summary is not intended to identify key or critical elements, delineate scope of particular embodiments or scope of claims. Its sole purpose is to present concepts in a simplified form as a prelude to the more detailed description that is presented later. In one or more embodiments described herein, systems, computer-implemented methods, apparatus and/or computer program products that facilitate learned predictability of humans being able to discriminate between odor mixtures.

In accordance with an embodiment, a system for compressing data during neural network training, comprises: a memory that stores computer executable components and neural network data; a processor that executes computer executable components stored in the memory, wherein the computer executable components comprise: a compilation component that compiles respective molecular descriptors regarding a first set of molecules.

In accordance with an aspect, a perception component learns human perception information related to olfactory perceptions of a first set of molecules and generates predictions of human olfactory perceptions of a second set of molecules.

In accordance with yet another aspect, a fitting component fits distance predictions from the perception component regarding the second set of molecules against measured correct classifications regarding the second set of molecules.

In accordance with yet another aspect, a vector component generates a perceptual vector distance between two olfactory targets.

DETAILED DESCRIPTION

Figure 1:
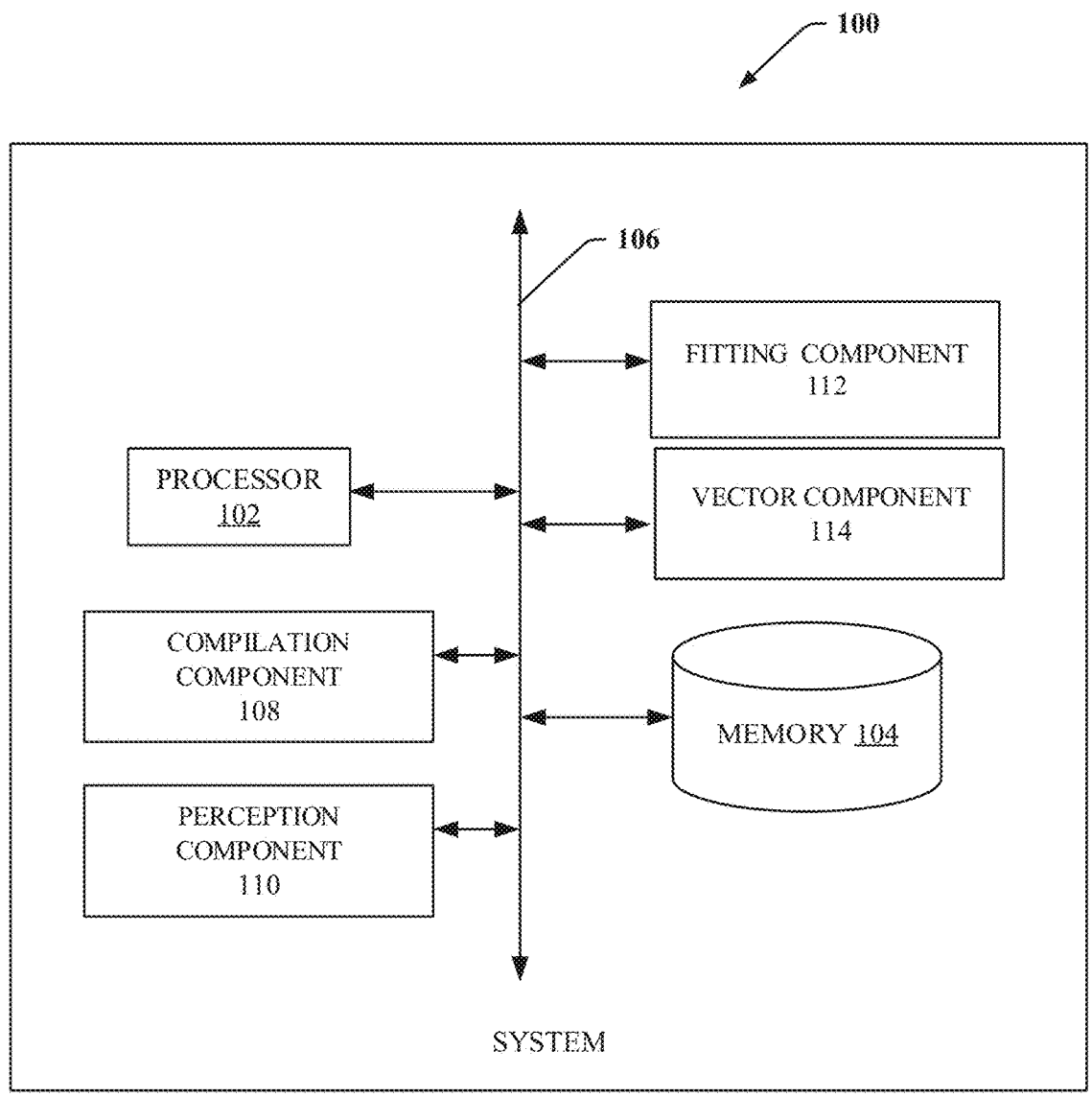
FIG. 1 illustrates a block diagram of an example system that can access data and process that data using variable computing components depicted in accordance with one or more embodiments described herein.

The following detailed description is merely illustrative and is not intended to limit embodiments and/or application or uses of embodiments. Furthermore, there is no intention to be bound by any expressed or implied information presented in the preceding Summary section, or in the Detailed Description section. One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident; however, in various cases, that the one or more embodiments can be practiced without these specific details.

There is interest in various colors, sounds and smells that humans can identify because such information can provide insight onto how human brains process senses. It is readily apparent as to how to humans identify colors or sounds as these stimuli can be defined by physical properties such as wavelength that can be mathematically measured. Currently it is known what respective ranges of wavelengths a human eye or ear can detect, and it is also understood how two such stimuli (e.g., such as colors red and blue) are arranged perceptually. However, it is substantially more difficult to measure or quantify the same for scent detection by humans because most 'olfactory stimuli' consist of mixtures of different and diverse components at different concentrations. For example, scent of a rose in general is produced by a mixture of over two hundred seventy five components. Human sense of smell is a primary factor upon which many industries rely upon to facilitate gauging desirability of items such as beverages, food and perfume. Sense of smell is intimately linked with memory; the olfactory bulb is a part of the brain that processes smell and interacts with regions of the brain that are responsible for storing emotional memories. Through a process of conditioned learning, a smell can become associated with an experience, person or time period with which it is repeatedly paired. Oftentimes, an individual may not be aware of a specific memory but have a positive or negative association with a scent not understanding why.

Odors generate from many sources and can be pleasant or intolerable. Various scents and aromas from coffee shops, perfumes and fragrances from flowers, are almost pleasant. In contrast, sewage plants, chemical factories and automobile exhaust produce odors that are deemed unpleasant. These frequently encountered odors have a feature in common, they are complex mixtures of odorants. An industry example of significance of olfactory odor perception is impact within an environment. In studies of air pollutants, for example, it is beneficial to be able to predict not only type of odor that will be produced by an industrial process, but also perceived odor strength outside the factory in nearby communities. Mathematical models for calculating dispersal of plumes of pollutants emanating from factories depend in part on molecular characteristics information that relate concentration of odorants to perceived odor intensity. At present, information available about types of constituents of many complex pollutants is scarce and even less is known about perceived intensity of such mixtures. Predicting strength and impact of pollutants on nearby communities is therefore difficult and inaccurate so a method to improve upon this type of void along with many others can be of significant value.

Embodiments within append upon an existing predictive model that is able to predict perceptual qualities (e.g., at least a subset of perceptual qualities—E.G. such as 21 for this example) of pure molecules (e.g., represented as MODEL P), from their structural properties as encoded in Dragon descriptors. Embodiments will extend its predictive ability to molecular mixtures (e.g., MODEL MM). Embodiments can utilize published datasets to imply that the model MM will predict human discriminability of odor mixtures (smell) at a higher accuracy rate than a previous model conducted by for example the Snitz Enhanced Method (e.g., MODEL SEM). Various embodiments described herein can incorporate inferred perceptual distance between odor mixtures through prediction of odor perceptual qualities and metric learning. The embodiments utilize predictions of human sensorial ratings to differentiate mixtures and employ metric learning to differentiate mixtures of odors. It is to be appreciated that the term chemical features as employed herein, for example, refers to properties of a molecule versus olfactory features which, for example relate to sensed aromatic properties of molecules.

Along with predicting human olfactory perceptual qualities of molecular mixtures, embodiments can be used to reverse engineer a process and generate a molecular structural compound from a set of perceived olfactory characteristics. For instance, if one wanted to obtain a molecular compound that smells like Perfume A, the embodiments could be manifested by using perceived descriptors of Perfume A and implementing artificial intelligence, machine learning or the like (e.g., neural networks, Support Vector Machines (SVMs), Bayesian networks, Hidden Markov Models (HMMs) . . . ) across respective data sets to produce a known molecular structure that would smell similar to Perfume A.

Various embodiments will take the previous model (P) to extend these predictions from pure molecules to molecular mixtures, the new model (MM) averages each molecular descriptor across the molecular components of the mixture and obtains structural characteristics of the mix. Then the embodiments can re-use model P (used for pure molecules) again to obtain values in the zero-one hundred interval for each of the twenty one perceptual descriptors, e.g.: Intensity, Pleasantness, Bakery, Sweet, Fish, Garlic, Cold, Sour, Burnt, Grass, Chemical, Fruit, Spices, Acid, Warm, Musky, Sweaty, Urinous, Decayed, Wood, Flower.

To test accuracy of these predictions, the model applies a task to these results consisting on distinguishing molecular mixtures through the scent(s) they produce. Embodiments define a Mahalanobis distance between mixtures which calculates a weighted Euclidian distance over the descriptors (e.g., at least a subset of descriptors—E.G. such as 21 for this example) where the initial weight value of 1 of each descriptor was changed and fitted in order to predict the percentage discriminability obtained in an experimental dataset. The Mahalanobis distance (MD) is distance between two points in multivariate space. In a regular Euclidean space, variables (e.g. x, y, z) are represented by axes drawn orthogonal to each other. The MD measures distances between points, even correlated points for multiple variables. It is to be appreciated that chemical features are not utilized to calculate the distance between molecules.

Concepts of the embodiments incorporate coefficients for the perceptual descriptors. An initial coefficient value was 1, but the model can be trained so that a result best matches values from incremental data, so essentially prediction is most correlated to percent of people able to differentiate the two mixtures. Coefficient values are then set from the training and now can be applied to any suitable data set.

The training of the MD with twenty-one example descriptors generated the below example coefficients:

| | |
|---|---|
| Intensity | 0.000719940220699876 |
| BAKERY | 0.0138228143227150 |
| SWEET | 0.00122436101055212 |
| FISH | 0.0497850544197713 |
| GARLIC | 0.00358620442521323 |
| COLD | 0.0347755400391788 |
| SOUR | 0.0169828569816300 |
| BURNT | 0.00430759902131422 |
| GRASS | 0.00848871765378457 |
| CHEMICAL | 0.000107958448313051 |

Other descriptors have a coefficient of zero (e.g., meaning they do not contribute to the MD) Pleasantness, Fruit, Spices, Acid, Warm, Musky, Sweaty, Urinous, Decayed, Wood, Flower.

Embodiments can generate a perceptual vector distance between two olfactory targets. Distance between two vectors can be calculated where distance equals root of sum of difference of squares e.g., Euclidian distance. Each of the differences of coordinates of each vector has a weight. That weight is generally the same but what changes are predictions of each of the mixtures. These weights are constant for mixtures, and for the mixture the embodiments utilize molecular features of molecules within the mixture to make a 0-100 prediction for each of the twenty-one perceptual descriptors. Then the same process for the other mixture is conducted, the model calculates the weighted difference between the two mixtures for each of the descriptors. That output will provide a value between 0 and 1, which is interpreted as a distance between the mixtures, or the percentage discriminability. One (1) represents a longest distance and zero (0) represents a shortest distance, and basically equal with respect to odor perception.

This system predicts the percent of people that can discriminate between two mixtures, so a value of (0.5) means 50% of the people.

Figure 3:
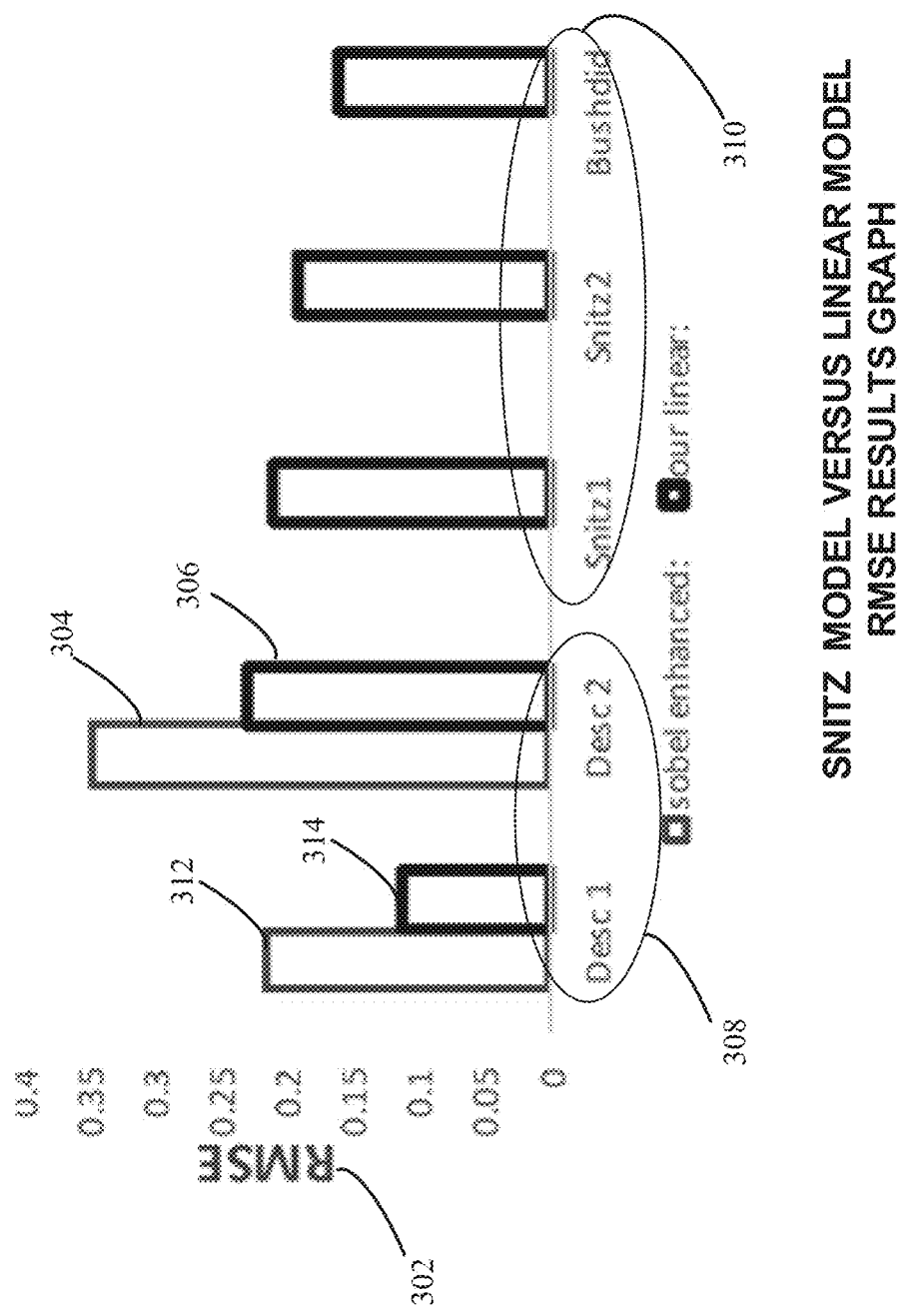
FIG. 3 illustrates a comparison of Snitz model error data to error data associated with an embodiment.

Results of the predictions in five different datasets have an average RMSE of 0.15 and embodiments outperform the previously existing method in these comparisons. The results are depicted in FIG. 3.

Example acts performed are:
1) Determine structural properties for each molecular mixture
2) Predict the twenty-one perceptual descriptors of each mixture
3) Perform the metric learning where Lasso regression was used with a Mahalanobis distance metric fit with a constant term. The Mahalanobis distance is learned on right fraction on the training dataset (Bushdid 2014), so that the values are fit to the [0,1] interval.
4) Predict using cross-validation on the Bushdid dataset and also on two unpublished datasets (Desc1 &2) and two previously published datasets (Snitz 1&2).

The Bushdid data consisted of mixtures of 10, 20, or 30 components drawn from a collection of 128 odorous molecules previously intensity-matched. In double-blind experiments, 26 subjects were presented with three odor vials, two of which contained the same mixture, whereas the third contained a different mixture. Each subject completed the same 264 discrimination tests. These tests result in a percentage of individuals (the right fraction) correctly distinguishing two mixtures.

From the RMSE (root mean squared error) chart, the data implies the embodiments within performed better than current processes. It is significant to note that these embodiments primary method is to use an algorithmic approach. Various embodiments first calculate values in perceptual space and then fit a metric using these values to differentiate between odor mixtures. The embodiments use the perceptual space and metric learning to differentiate odor mixtures.

FIG. 1 illustrates a block diagram of an example system 100 that can access data and process that data using variable computing components depicted in accordance with one or more embodiments described herein. The system 100 can facilitate a process of assessing and identifying a large amount of various forms of data, and using machine learning, training a neural network or other type of model. The system 100 can also generate predictive recommendations to an individual level resulting in a context in accordance with one or more embodiments described herein. Aspects of systems (e.g., system 100 and the like), apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. Repetitive description of like elements employed in one or more embodiments described herein is omitted for sake of brevity.

System 100 can optionally include a server device, one or more networks and one or more devices (not shown). The system 100 can also include or otherwise be associated with at least one processor 102 that executes computer executable components stored in memory 104. The system 100 can further include a system bus 106 that can couple various components including, but not limited to, a compilation component 108 that compiles respective molecular descriptors regarding a first set of molecules, a perception component 110 that learns human perception information related to olfactory perceptions of the first set of molecules, and generates predictions of human olfactory perceptions of a second set of molecules, a fitting component 112 that fits distance predictions from the perception component regarding the second set of molecules against measured correct classifications regarding the second set of molecules, and a vector component 114 that generates a perceptual vector distance between two olfactory targets.

The system 100 can be any suitable computing device or set of computing devices that can be communicatively coupled to devices, non-limiting examples of which can include, but are not limited to, a server computer, a computer, a mobile computer, a mainframe computer, an automated testing system, a network storage device, a communication device, a web server device, a network switching device, a network routing device, a gateway device, a network hub device, a network bridge device, a control system, or any other suitable computing device. A device can be any device that can communicate information with the system 100 and/or any other suitable device that can employ information provided by system 100. It is to be appreciated that system 100, components, models or devices can be equipped with communication components (not shown) that enable communication between the system, components, models, devices, etc. over one or more networks.

In accordance with the system 100, the memory 104 can store computer executable components executable by the processor 102. The compiling component 108 can also compile a library of a plurality of indexed olfactory descriptors (e.g., molecular and sematic) and chemoinformatic vectors. Perception component 110 can also act as a learning component. Vector component 114 generates a perceptual vector based at least in part upon a plurality of target sematic descriptors and also generates a distance function using regression.

The various components of system 100 can be connected either directly or via one or more networks. Such networks can include wired and wireless networks, including, but not limited to, a cellular network, a wide area network (WAN) (e.g., the Internet), or a local area network (LAN), non-limiting examples of which include cellular, WAN, wireless fidelity (Wi-Fi), Wi-Max, WLAN, radio communication, microwave communication, satellite communication, optical communication, sonic communication, or any other suitable communication technology. Moreover, the aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components can be combined into a single component providing aggregate functionality. The components can also interact with one or more other components not specifically described herein for the sake of brevity, but known by those of skill in the art.

The subject computer processing systems, methods apparatuses and/or computer program products can be employed to solve new problems that arise through advancements in technology, computer networks, the Internet and the like.

Figure 2:
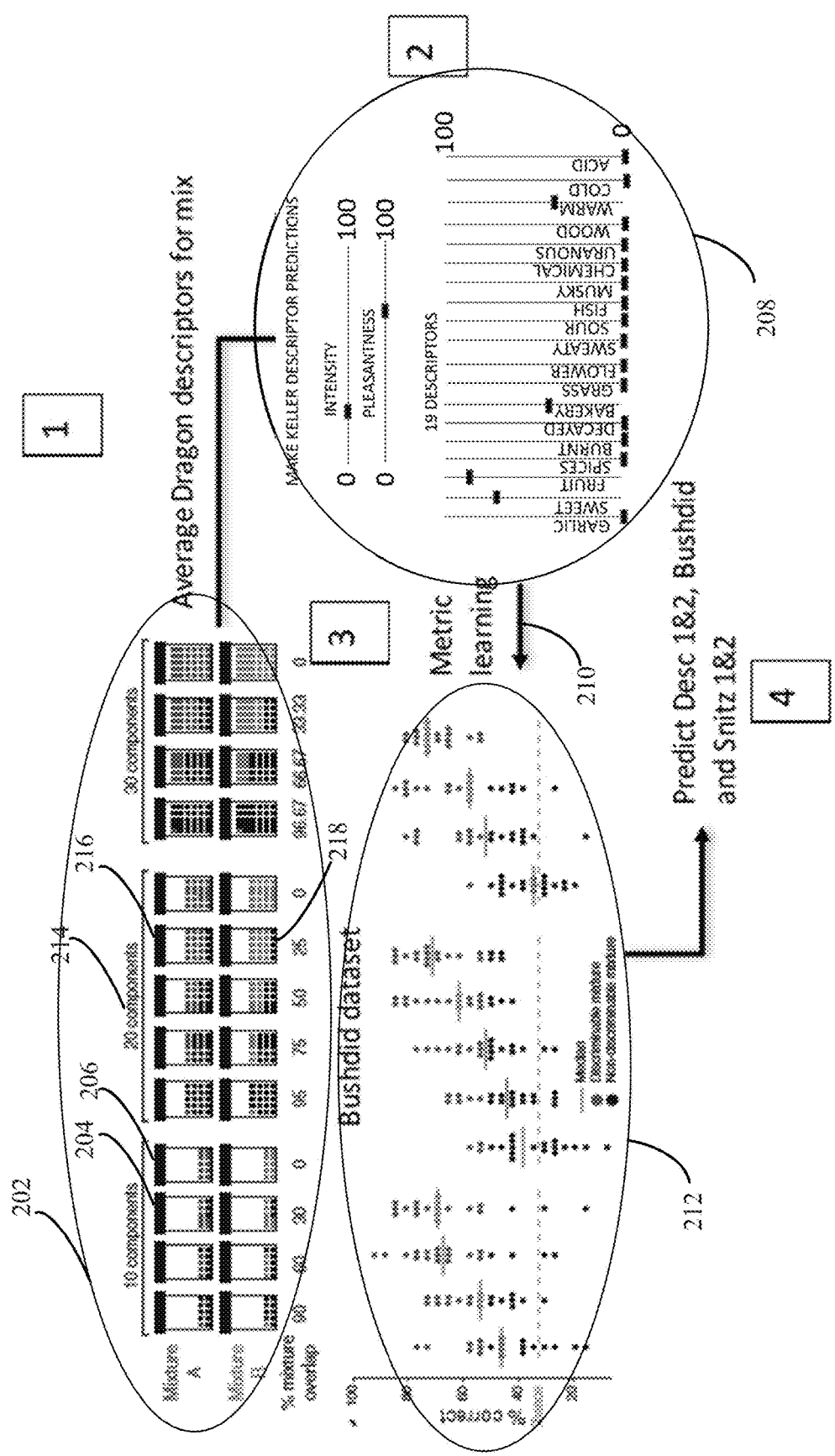
FIG. 2 illustrates a process that facilitates predicting perceptual olfactory qualities of molecular mixtures and perceptual distance between odor mixtures based on structural properties in accordance with an embodiment.

FIG. 2 illustrates four exemplary acts in connection with an embodiment. At act 1, initial mixture sample components 202 that are utilized. In this example, there are multiple samples that make up the Bushdid data set. There are two mixtures (Mixture A and Mixture B), each mixture has three categories (10 components, 20 components and 30 components). Mixture A and Mixture B have four containers in the 10 component category, five containers in the 20 component category and four in the 30 component category. The containers can have a variant concentration level of Mixture A or B and a non-discriminable mixture within each container. For instance, a 10 component container 204 has a concentration of 70% Mixture A and 30% of a non-discriminable mixture. Each container in the 10 components category is identified as in 206. In the container category 214, each container houses 20 components, each container in this category (such as for example 216) represents a 20 component container with a variable concentration of mixture A and of a non-discriminable mixture. Container 218 represents a 20 component container with a variable concentration of mixture B and of a non-discriminable mixture. The embodiments average each molecular descriptor across molecular components of the mixture obtaining structural characteristics of the mix, then the embodiments employ the same model (as previously identified as MODEL P) to obtain values between a 0-100 interval for each of the perceptual descriptors (e.g., at least a subset of descriptors—E.G. such as 21 for this example). This is act 2 in which the perceptual descriptors prediction results are shown by reference 208. The descriptors have values that are listed within a range of 0-100. In act 3, a metric model 210 is used to fit distance predictions to actual measured correct classifications identified by humans. Act 4 is a testing sample result(s) 212, that derive from the Bushdid data set.

FIG. 3 illustrates test data error percentages using a root mean squared error graph 302. Root Mean Square Error (RMSE) measures how much error there is between two data sets. In other words, it compares a predicted value and an observed or known value. It is a measure of how well the subject model performed. It does this by measuring difference between predicted values and the actual values. This chart represents a comparison of the embodiments model against the Snitz model using different data sets. For example, in a model that receives an input X and the model predicts 10, but the actual value is 5; the difference between prediction of 10 and the actual observation of 5 is the error term: (y_prediction−y_actual). The error term is significant because it is desired to minimize error so that predictions are close to actual values. In an example case, using the square root of the squared difference (RMSE), the equation is as below:

$$RMSE = \sqrt{\frac{\sum_{i=1}^{N}(Predicted_i - Actual_i)^2}{N}}$$

In a satisfactory model, the RMSE should be close for both testing data and training data. If the RMSE for testing data is higher than the training data, there is a high chance that the model overfit. In other words, the model performed worse during testing than training. In general, RMSE is a commonly used metric and serves well as a general purpose error metric. The red RMSE value block 314 reflects the embodiment has an error % of approximately 0.1 while the blue Snitz method 312 had an approximate 0.22% value which imply a more accurate result from the embodiments method. The red RMSE value block 306 reflects the embodiment has an error % of approximately 0.25 while the blue Snitz method 304 had an approximate 0.35% value which also implies a more accurate result from the embodiments method. The results shown on this graph are based upon various data sets such as Snitz1, Snitz2, Bushdid (310) and two others that are unpublished (308). The embodiments linear model clearly depicts low RMSE levels below 0.25 RMSE for each comparison. The lower RMSE level could be a major contributor to any decision making regarding use of this model for many applications.

Figure 4:
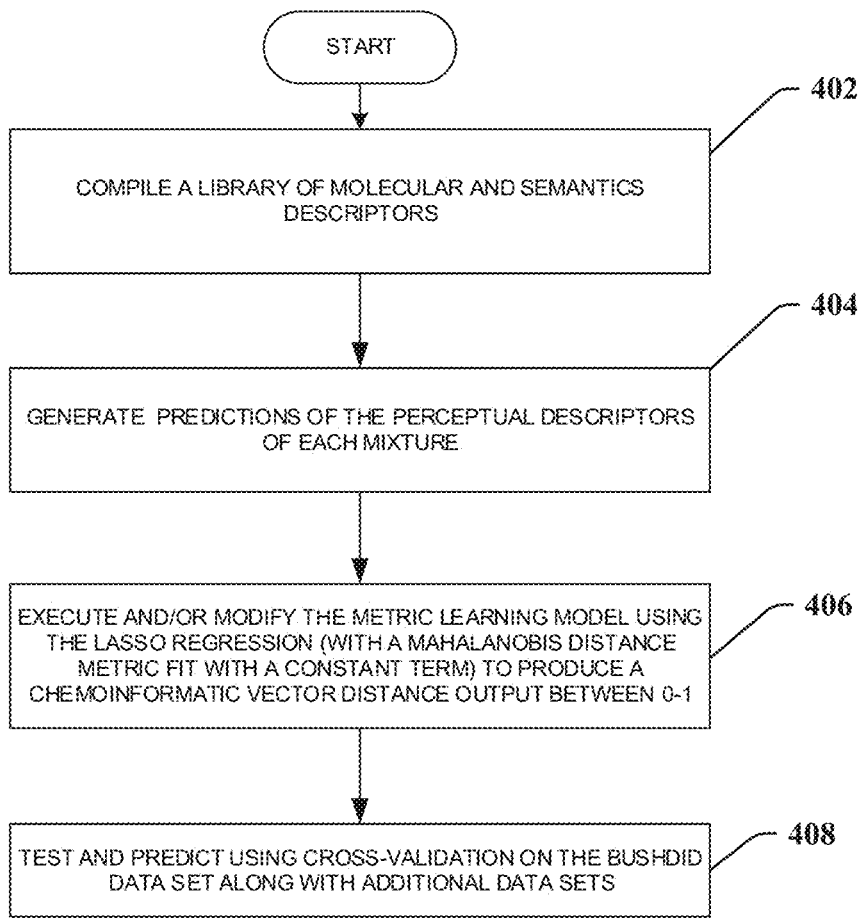
FIG. 4 illustrates a methodology for predicting human discriminability of odor mixtures in accordance with one or more embodiments.

FIG. 4 is a flowchart of various acts steps in a non-limiting embodiment. Act 1 is to compile a library of olfactory molecular and semantic descriptors as in 402. Compiling a library of olfactory molecular and sematic descriptors refers to Dragon descriptors which are commonly used in the scientific forum and in scientific studies. Dragon is an application for the calculation of molecular descriptors and these descriptors can be used to evaluate molecular structure-activity or structure-property relationships, as well as for similarity analysis and high-throughput screening of molecule databases. Dragon is a world-wide used application and calculates about 5,270 molecular descriptors, covering most of the various theoretical approaches. The list of descriptors includes the simplest atom types, functional groups and fragment counts, topological and geometrical descriptors, three-dimensional descriptors, but also several properties estimation and drug-like and lead-like alerts (such as the Lipinski's alert). The table listing below provides an example.

| List of molecular descriptors calculated by Dragon | | | |
|---|---|---|---|
| ID | Name | Description | Block |
| 1 | MW | Molecular weight | Constitutional indices |
| 2 | AMW | Average Molecular weight | Constitutional indices |
| 3 | Sv | Sum of atomic van der Waals volumes | Constitutional indices |
| 4 | Se | Sum of atomic Sanderson electronegativities | Constitutional indices |
| 5 | Sp | Sum of atomic polarizabilities | Constitutional indices |

Act 2 at 404 generates predictions of at least a subset of perceptual qualities (e.g., 21) for this example of each mixture; this is based off a same process as used for prior Model P described earlier in this document. Act 3 at 406 is executing a metric learning model using Lasso regression with a Mahalanobis distance metric with a constant term. Act 4 at 408 tests and predicts human discriminability of odor mixtures using various data sets. As previously mentioned, it is significant to note the difference between chemical features (properties of the molecule) versus olfactory features which are the sensed aromatic properties of the molecules when referring to these embodiments.

Figure 5:
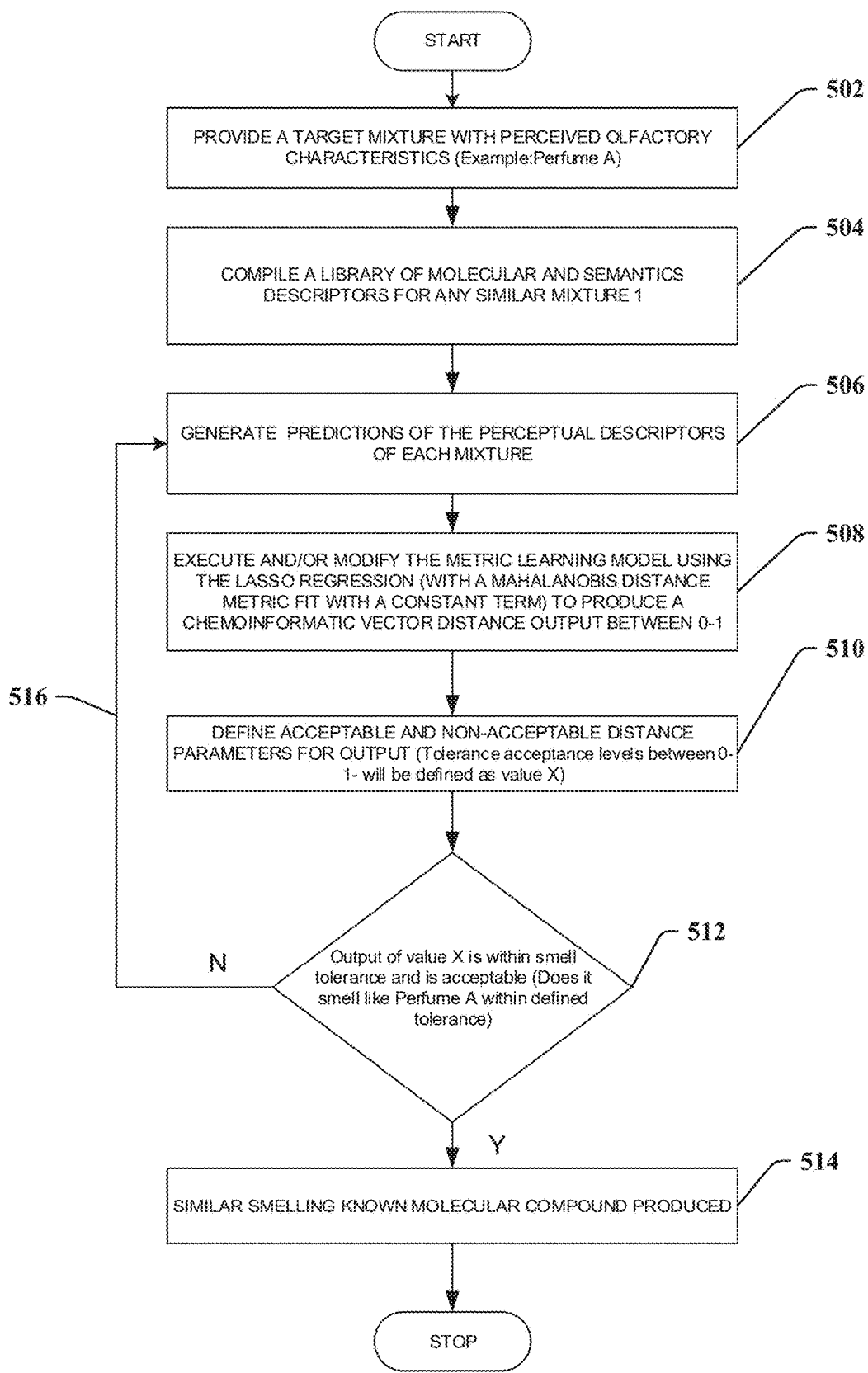
FIG. 5 illustrates the basic embodiments methodology to assess odor perception in commercial industry in accordance with one or more embodiments.

FIG. 5 is an example flowchart depicting an example of how the embodiments could be utilized to develop a molecular mixture that could produce a similar odor to an existing target odor. In this example, 502 is the target mixture that embodiments can clone (for this example, Perfume A which has an unknown molecular mixture). For this mixture a list of semantic descriptors are assigned based on perceived smell by a test group. Then a similar molecular structure 504 is selected and processed through a learning process that can generate a known molecular compound that will smell very similar to Perfume A itself. Act 506 in the process will generate predictions of the (e.g., at least a subset of perceptual qualities—E.G. such as 21 for this example) perceptual descriptors and act 508 can use this data along with the learning algorithm to start fitting distances between Perfume A and our molecular compound with a value level of 0-1. Depending on what is defined as an acceptable similar scent to Perfume A, the value is then processed further at act 510. If the test group accepts the smell at act 512 then the molecular compound is defined at that point at act 514. If the scent is not acceptable, different compounds can be tried. As an alternative embodiment the perceived characteristics can be sent back into the model at act 516 for re-learning and producing a new compound that is more identical to Perfume A. This feedback process can be iterative and constantly lead to a narrower and more precise final molecular structure closer to the target as the learning algorithm can accept and digest pertinent data for various instances of the feedback loop.

Figure 6:
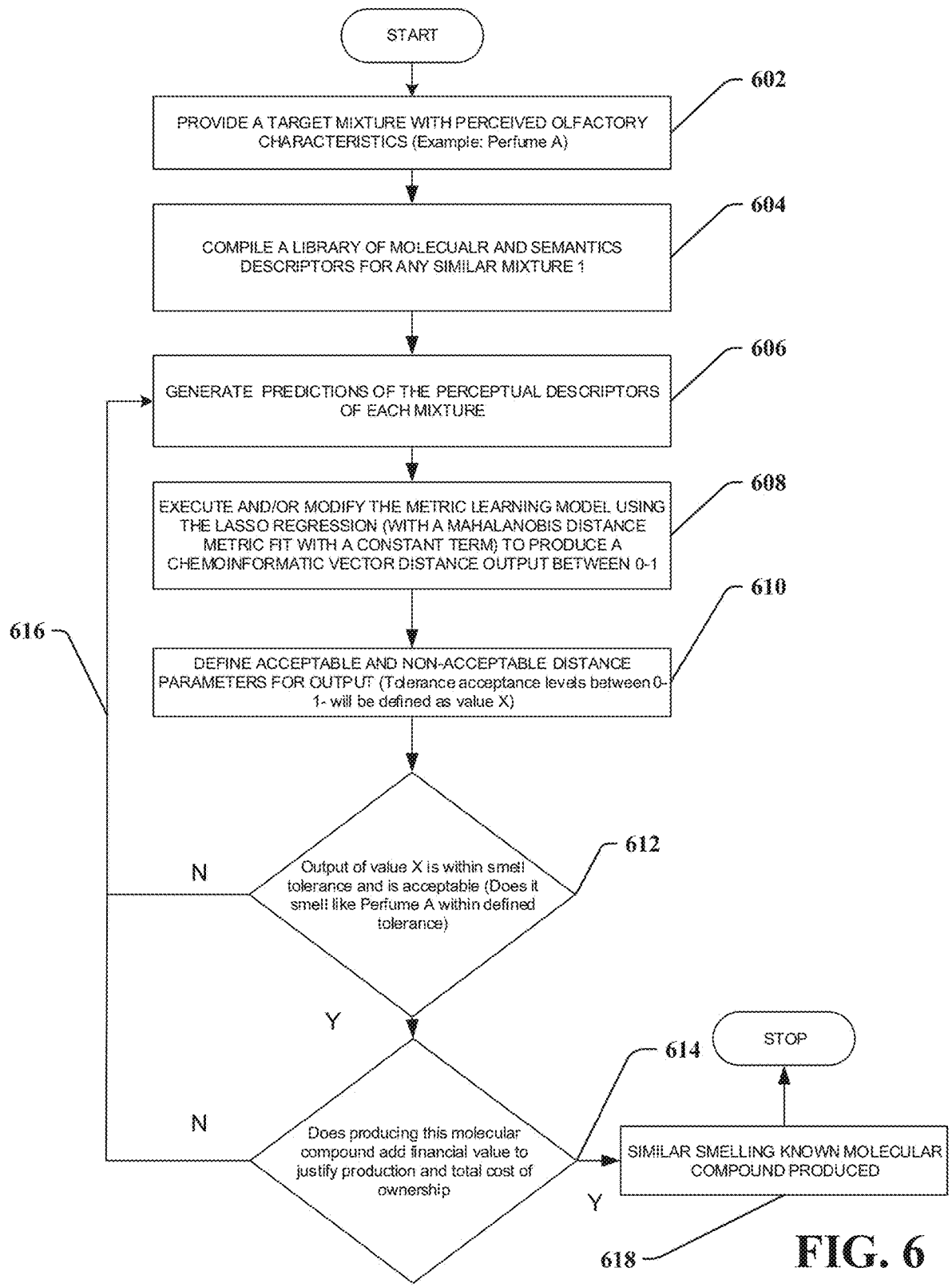
FIG. 6 illustrates the basic embodiments methodology that can be utilized to produce various similar compounds based on cost structure in commercial industry in accordance with one or more embodiments

FIG. 6 illustrates an example methodology that can be utilized to produce various similar compounds based on cost structure in commercial industry in accordance with one or more embodiments. There are potentially many applications using predictive odor perception from molecular structure in commercial industry. The embodiments build a model to predict odor qualities of a certain molecules (mixtures), e.g., by using its structure and molecular descriptors. The embodiments can utilize chemoinformatics, which is a new discipline at the center of computer science and chemistry designed to extract, at different scales, informative features from structure of molecule(s). Embodiments can provide fundamental insights into how chemicals are transformed into a smell percept in the brain; how the brain perceives odors. Along with this fundamental biological understanding, the ability to reverse-engineer smells by designing molecules can be a major technological advance for perfume and flavor industries. The global flavors and fragrances market is expected to grow over the next decade and a fundamental understanding of olfactory predictive models based on chemoinformatics can provide significant advantage for organizations in these vertical industries. While flavors and fragrances can make up a small percent of cost of a finished product, smell can be a key differentiator in product selection by consumers. It is known that scent can be an important sense tied to memory and emotion, with a direct line pairing unique scents with product experiences can build deep memories and connections with a brand, promoting both long-term loyalty and sales. Many can remember the smell of a strong laundry detergent used in the past, even resulting in multiple generations of people purchasing the same product. Extending beyond scents of individual products, ambient smells in a shopping environment have also proven to influence consumer behavior. According to past studies, it was demonstrated that the "temperature" of scents in a store has powerful effect on what, and how much, customers buy. Customers who smelled "warm" fragrances (like cinnamon) are typically more likely to purchase items they thought raised their personal status. Compared to those smelling "cool" scents, or not smelling any scent. Not limited to developing food flavors; the same approach can be taken for creating new flavors and odors in consumer products such as cleaning and personal hygiene products. By applying a clear predictive approach, a company could shorten time it takes to create new or custom-tailored odors. Predictive models in connection embodiments can guide design of new molecules for fields such as perfumery, flavor science, or other industrial applications. This flow is similar to FIG. 5, but includes a cost comparison strategy. In this example, at act 602 target mixture is selected that the embodiment will try to clone (for this example Perfume A which has an unknown molecular mixture). For this mixture a list of semantic descriptors are assigned based on perceived smell by a test group. Then a similar molecular structure at act 604 is selected and put through a learning process that will generate a known molecular compound that will smell very similar to Perfume A. At act 606, the process will generate predictions of (e.g., at least a subset of perceptual qualities—E.G. such as 21 for this example) perceptual descriptors and at act 608 can use this data along with the learning algorithm to fit distances between Perfume A and the subject molecular compound, e.g., with a value level of 0-1. Depending on what is defined as an acceptable similar scent to Perfume A, the value is then processed further at act 610. If the test group accepts the smell at act 612 and the producing the new known molecular compound is deemed cost worthy act 614 (e.g., based on various decision making factors) then the molecular compound is defined at that point at act 618. If the scent is not acceptable or it is cost prohibitive to produce this structure, then new compounds can be tried or the perceived characteristics can be sent back into the learning model at act 606 for re-learning and producing a new compound that is acceptable as far as similar smell to Perfume A while also being cost effective.

Figure 7:
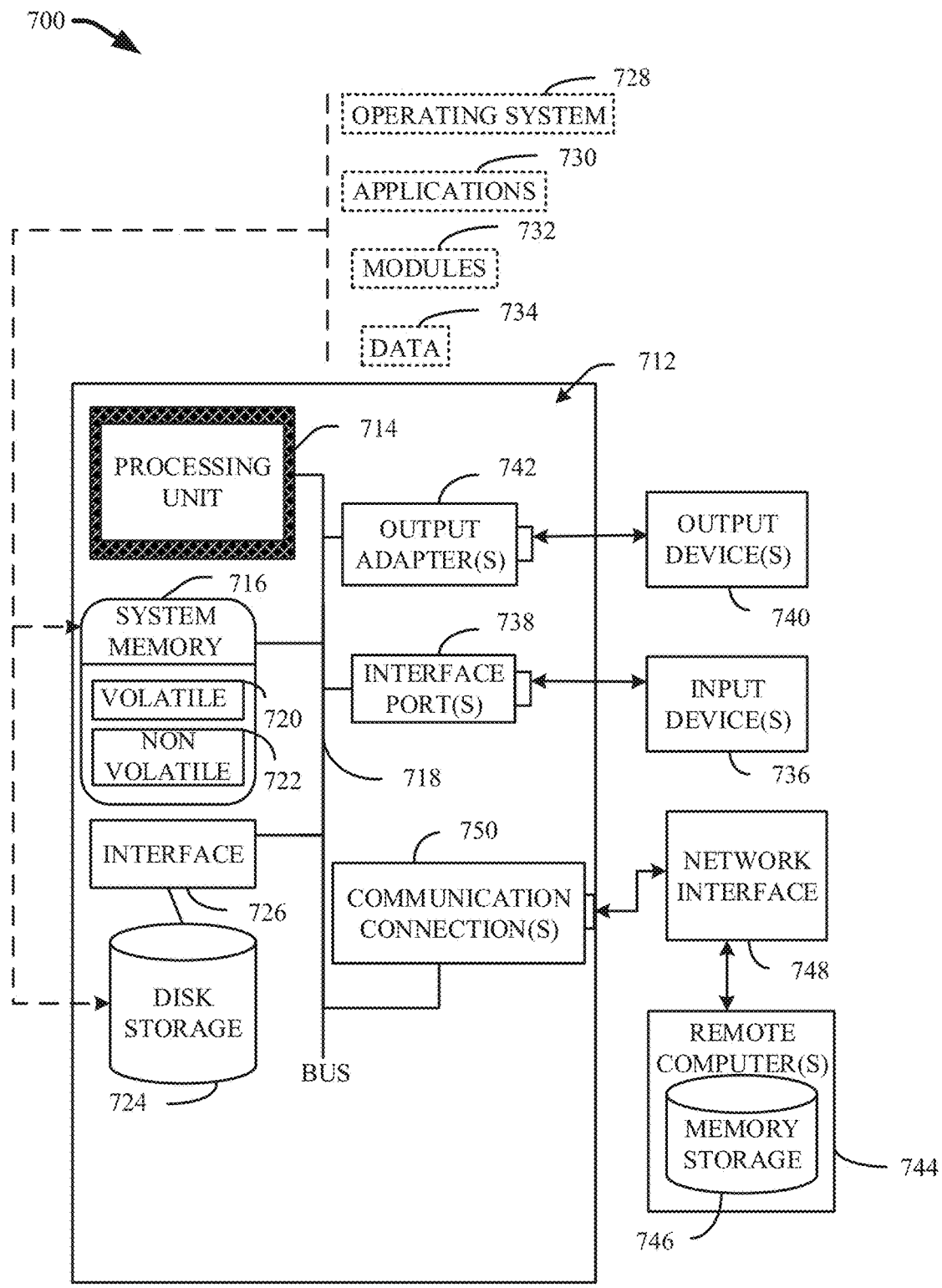
FIG. 7 is a schematic diagram of an example operating environment in accordance with one or more implementations described herein.

FIG. 7 as well as the following discussion are intended to provide a general description of a suitable environment in which the various aspects of the disclosed subject matter can be implemented. FIG. 7 illustrates a block diagram of an example, non-limiting operating environment in which one or more embodiments described herein can be facilitated. Repetitive description of like elements employed in other embodiments described herein is omitted for sake of brevity.

A suitable operating environment 700 for implementing various aspects of this disclosure can also include a computer 712. The computer 712 can also include a processing unit 714, a system memory 716, and a system bus 718. The system bus 718 couples system components including, but not limited to, the system memory 716 to the processing unit 714. The processing unit 714 can be any of various available processors. Dual microprocessors and other multiprocessor architectures also can be employed as the processing unit 714. The system bus 718 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1094), and Small Computer Systems Interface (SCSI). The system memory 716 can also include volatile memory 720 and nonvolatile memory 722. The basic input/output system (BIOS), containing the basic routines to transfer information between elements within the computer 712, such as during start-up, is stored in nonvolatile memory 722. By way of illustration, and not limitation, nonvolatile memory 722 can include read only memory (ROM), programmable ROM (PROM), electrically programmable ROM (EPROM), electrically erasable programmable ROM (EEPROM), flash memory, or nonvolatile random-access memory (RAM) (e.g., ferroelectric RAM (FeRAM). Volatile memory 720 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 712 can also include removable/non-removable, volatile/nonvolatile computer storage media. FIG. 7 illustrates, for example, a disk storage 724. Disk storage 724 can also include, but is not limited to, devices like a magnetic disk drive, floppy disk drive, tape drive, Jaz drive, Zip drive, LS-100 drive, flash memory card, or memory stick. The disk storage 724 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 724 to the system bus 718, a removable or non-removable interface is typically used, such as interface 726. FIG. 7 also depicts software that acts as an intermediary between users and the basic computer resources described in the suitable operating environment 700. Such software can also include, for example, an operating system 728. Operating system 728, which can be stored on disk storage 724, acts to control and allocate resources of the computer 712. System applications 730 take advantage of the management of resources by operating system 728 through program modules 732 and program data 734, e.g., stored either in system memory 716 or on disk storage 724. It is to be appreciated that this disclosure can be implemented with various operating systems or combinations of operating systems. A user enters commands or information into the computer 712 through input device(s) 736. Input devices 736 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 714 through the system bus 718 via interface port(s) 738. Interface port(s) 738 include, for example, a serial port, a parallel port, a game port, and a universal serial bus (USB). Output device(s) 740 use some of the same type of ports as input device(s) 736. Thus, for example, a USB port can be used to provide input to computer 712, and to output information from computer 712 to an output device 740. Output adapter 742 is provided to illustrate that there are some output devices 740 like monitors, speakers, and printers, among other output devices 740, which require special adapters. The output adapters 742 include, by way of illustration and not limitation, video and sound cards that provide a means of connection between the output device 740 and the system bus 718. It should be noted that other devices and/or systems of devices provide both input and output capabilities such as remote computer(s) 744.

Computer 712 can operate in a networked environment using logical connections to one or more remote computers, such as remote computer(s) 744. The remote computer(s) 744 can be a computer, a server, a router, a network PC, a workstation, a microprocessor based appliance, a peer device or other common network node and the like, and typically can also include many or all the elements described relative to computer 712. For purposes of brevity, only a memory storage device 746 is illustrated with remote computer(s) 744. Remote computer(s) 744 is logically connected to computer 712 through a network interface 748 and then physically connected via communication connection 750. Network interface 748 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection (s) 750 refers to the hardware/software employed to connect the network interface 748 to the system bus 718. While communication connection 750 is shown for illustrative clarity inside computer 712, it can also be external to computer 712. The hardware/software for connection to the network interface 748 can also include, for exemplary purposes only, internal and external technologies such as, modems including regular telephone grade modems, cable modems and DSL modems, ISDN adapters, and Ethernet cards.

Embodiments of the present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in one or more computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, to perform aspects of the present invention.

Aspects of the present invention are described herein with reference to flowchart illustrations and/or block diagrams of methods, apparatus (systems), and computer program products according to embodiments of the invention. It will be understood that one or more blocks of the flowchart illustrations and/or block diagrams, and combinations of blocks in the flowchart illustrations and/or block diagrams, can be implemented by computer readable program instructions. These computer readable program instructions can be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, one or more blocks in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that one or more block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a server computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products, and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system for compressing data, comprising:
    a memory that stores computer executable components and neural network data;
    a processor that executes computer executable components stored in the memory, wherein the computer executable components comprise:
        a compilation component that compiles respective molecular descriptors regarding a first set of molecules;
        a perception component that learns human perception information related to olfactory perceptions of the first set of molecules, and generates predictions of human olfactory perceptions of a second set of molecules;
        a fitting component that fits distance predictions from the perception component regarding the second set of molecules against measured correct classifications regarding the second set of molecules; and
        a vector component that generates a perceptual vector distance between two olfactory targets that respectively comprise at least one of: the first set of molecules or the second set of molecules.

2. The system of claim 1, further comprising an indexing component that generates a library of olfactory descriptors that include chemoinformatic descriptors and semantic descriptors.

3. The system of claim 2, wherein the library comprises chemoinformatic vectors.

4. The system of claim 1, wherein the vector component generates the perceptual vector based at least in part upon a plurality of source chemoinformatic vectors.

5. The system of claim 1, wherein the vector component generates the perceptual vector based at least in part upon a plurality of target semantic descriptors.

6. The system of claim 1, wherein the vector component generates a distance function or distance matrix using regression.

7. The system of claim 1, wherein a distance function is fitted across a set of subjects able to distinguish odor mixture through smell.

8. The system of claim 1, wherein the vector component generates a function or projection matrix and a perceptual distance between an indexed olfactory descriptor and a olfactory target descriptor.

9. A computer-implemented method, comprising:
    compiling, by a device operatively coupled to a processor, respective molecular descriptors regarding a first set of molecules;
    learning, by the device, human perception information related to olfactory perceptions of the first set of molecules, and generates predictions of human olfactory perceptions of a second set of molecules;
    fitting, by the device, distance predictions from the perception component regarding the second set of molecules against measured correct classifications regarding the second set of molecules; and generating, by the device, a perceptual vector distance between two olfactory targets that respectively comprise at least one of: the first set of molecules or the second set of molecules.

10. The computer-implemented method of claim 9, further comprising:
generating, by the device, a library of olfactory descriptors that include molecular descriptors and semantic descriptors.

11. The computer-implemented method of claim 9, further comprising:
generating, by the device, the perceptual vector based at least in part upon a plurality of source chemoinformatic vectors.

12. The computer-implemented method of claim 9, further comprising:
generating, by the device, the perceptual vector based at least in part upon a plurality of target semantic descriptors.

13. The computer-implemented method of claim 9, further comprising:
generating, by the device, a distance function or distance matrix using regression.

14. The computer-implemented method of claim 9, further comprising:
fitting, by the device, a distance function across a set of subjects able to distinguish odor mixture through smell.

15. The computer-implemented method of claim 9, further comprising:
generating, by the device, a function or projection matrix and a perceptual distance between an indexed olfactory descriptor and an olfactory target descriptor.

16. A computer program product comprising a computer readable storage medium having program instructions embodied therewith, the program instructions executable by a processor to cause the processor to:
compile respective molecular descriptors regarding a first set of molecules;
learn human perception information related to olfactory perceptions of the first set of molecules, and generates predictions of human olfactory perceptions of a second set of molecules;
fit distance predictions from the perception component regarding the second set of molecules against measured correct classifications regarding the second set of molecules; and
generate a perceptual vector distance between two olfactory targets that respectively comprise at least one of: the first set of molecules or the second set of molecules.

17. The computer program product of claim 16, the program instructions further causing the processor to:
generate a library of olfactory descriptors that include molecular descriptors and semantic descriptors.

18. The computer program product of claim 16, the program instructions further causing the processor to:
generate the perceptual vector based at least in part upon a plurality of source chemoinformatic vectors.

19. The computer program product of claim 16, the program instructions further causing the processor to:
generate the perceptual vector based on the values of the semantic descriptors.

20. The computer program product of claim 16, the program instructions further causing the processor to:
generate a function or projection matrix and a perceptual distance between an indexed olfactory descriptor and an olfactory target descriptor.

* * * * *